United States Patent [19]

Pfitzner et al.

[11] 3,936,445

[45] Feb. 3, 1976

[54] PROCESS FOR THE PRODUCTION OF IRON COMPLEXES OF TETRAAZAANNULENES

[75] Inventors: Helmut Pfitzner, Neckargemuend; Walter Dammert, Frankenthal, both of Germany

[73] Assignee: Badische Anilin- & Soda-Fabrik Aktiengesellschaft, Ludwigshafen (Rhine), Germany

[22] Filed: Mar. 14, 1974

[21] Appl. No.: 451,034

Related U.S. Application Data

[63] Continuation-in-part of Ser. No. 384,628, Aug. 1, 1973, abandoned.

[30] Foreign Application Priority Data

July 4, 1973 Germany............................ 2333925

[52] U.S. Cl....... 260/239 DD; 252/430; 252/431 N; 260/307 H

[51] Int. Cl.$^2$................ C07D 257/00; C07D 259/00
[58] Field of Search............................ 260/239 DD

[56] References Cited

OTHER PUBLICATIONS

Hiller et al., "Liefig's Snn. Chem.", Vol. 717, pp. 137–147, (1968).

*Primary Examiner*—Donald G. Daus
*Assistant Examiner*—D. B. Springer
*Attorney, Agent, or Firm*—Johnston, Keil, Thompson & Shurtleff

[57] ABSTRACT

Process for the production of iron complexes of tetraazaannulenes starting from isoxazole, o-phenylene diamines and iron compounds. The process yields the iron complexes in good yields and a state of high catalytic activity for oxidation processes.

3 Claims, No Drawings

PROCESS FOR THE PRODUCTION OF IRON COMPLEXES OF TETRAAZAANNULENES

This application is a continuation-in-part of U.S. application Ser. No. 384,628, filed on Aug. 1, 1973 now abandoned.

The invention relates to a process for the production of compounds having the formula (I):

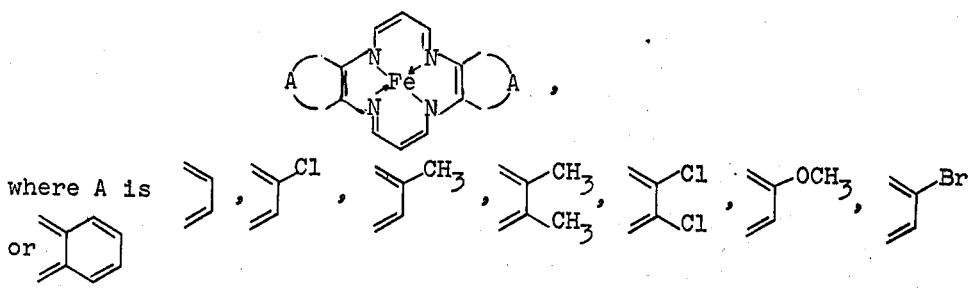

comprising reacting one mole of isoxazole of the formula

with one mole of a diamine of the formula (II):

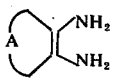

and simultaneously or subsequently with about ½ mole of an iron compound selected from iron salts of organic mono- or dicarboxylic acids selected from formic, acetic, propionic, glyoxylic, lactic, malic, gluconic, oxalic, malonic, succinic, maleic, fumaric, tartaric and citric acid, and iron acetyl acetonate, iron carbonate and iron hydroxides.

Examples of diamines of the formula (II) are: 2,3-diaminonaphthalene, 4-chloro-1,2-diaminobenzene, 4-bromo-1,2-diaminobenzene, 4-methoxy-1,2-diaminobenzene, 4,5-dimethyl-1,2-diaminobenzene, 4,5-dichloro-1,2-diaminobenzene, and, preferably, 4-methyl-1,2-diaminobenzene and o-phenylenediamine.

Iron compounds which yield metal include for example iron salts of weak inorganic or organic acids such as iron carbonate, iron acetate, iron lactate, iron oxalate, iron citrate, iron tartrate or iron gluconate. Iron salts of polybasic organic acids and those of oxycarboxylic acids are generally particularly suitable. Compounds containing iron in complex combination, for example iron acetylacetonates, are also particularly suitable because of the volatility of the ligands in the formation of the annulenes. Iron hydroxides may also be used for the preparation of the compounds of formula (I).

Examples of iron compounds are: iron formate, acetate, propionate, glycolate, lactate, maleate, gluconate, oxalate, malonate, succinate, maleinate, fumarate, tartrate, citrate, acetylacetonate, carbonate and hydroxide. Of particular interest are iron glycolate, tartrate, oxalate, citrate, lactate, acetylacetonate, carbonate, hydroxide and preferably iron acetate.

The iron complexes of the formula I may be prepared by dissolving isoxazole and the compound of the formula (II) in a solvent and slowly adding the iron-yielding compound or, preferably, suspending the compound of the formula (II) and the iron compound in a diluent and slowly adding the isoxazole. The formation of the complexes of the formula I proceeds exothermically and the reaction can be controlled by the rate of addition of the third compound.

Suitable reaction temperatures are 40° to 120°C, preferably 70° to 100°C. The mole ratio of the reactants is 2 : 2 : 1 (compound of formula (II): isoxazole : iron compound). Slight deviations from this ratio have no detrimental effect.

Examples of solvents or diluents suitable as reaction medium are: alcohols, such as methanol, ethanol, propanol or isobutanol, glycols and glycol ethers such as ethylene glycol and diethylene glycol and their monomethyl, monoethyl or monobutyl ethers, tetrahydrofuran, dioxane, dimethylformamide or N-methylpyrrolidone.

When the reaction is over the sparingly soluble iron complex compound is separated from the reaction mixture and worked up; if necessary it can be purified by washing and boiling up with a solvent.

Details of the production may be seen in the Examples.

The sparingly soluble reddish brown to black iron complex compounds are not as a rule obtained analytically pure when sparingly soluble iron compounds such as hydroxides, carbonates, acetates or oxalates are used, but their catalytic activity is excellent.

The new metal complex compounds may be subjected to conditioning operations in which comminution, dispersion or recrystallization processes takes place for use as catalysts. In accordance with the purpose for which the iron complex compounds are used they may be used in pure form or in the form of formulations on or in carrier materials of great variety, for example activated carbon, carbon black, diatomite, silica gel, aluminum oxide, as substances used as ion exchangers or plastics. The purpose decides the most suitable form.

Parts and percentages hereinafter are by weight.

EXAMPLE 1

21.6 parts of o-phenylenediamine is dissolved at ambient temperature in 100 parts by volume of dimethylformamide and then 13.8 parts of isoxazole (dissolved in alcohol) is added slowly. After 15 minutes at 30°C 11.6 parts of iron carbonate is added and the mixture is heated for two hours at 120°C, suction filtered, washed with dimethylformamide and methanol and dried. 9.2 parts of a dark brown powder is obtained which has high catalytic activity.

EXAMPLE 2

24.4 parts of 1-methyl-3,4-diaminobenzene is dissolved at ambient temperature in 100 parts by volume of dimethylformamide and 13.8 parts of isoxazole (in solution in alcohol) is slowly added. After 15 minutes at 30°C 19 parts of basic iron acetate is added and the mixture is heated for two hours at 120°C. After processing as described in Example 1 about 6 parts of a dark brown powder is obtained which has high catalyzing activity.

EXAMPLE 3

A mixture of 120 parts of isobutanol, 15.2 parts of o-phenylenediamine and 15.4 parts of basic iron (III) acetate is heated for 45 minutes at 95° to 100°C. A solution of 9.65 parts of isoxazole in approx. 25 parts of isobutanol is dripped into this mixture in such a manner that the temperature remains between 95° and 100°C without heating. The reaction mixture is subsequently kept for 4 hours at from 95° to 100°C and filtered hot, and the residue is washed with isobutanol and dried at 60°C. 18.8 parts of a black powder is obtained which has extremely high catalytic activity.

Starting from isoxazole the following further complexes which also have high catalytic activity are obtained analogously to Examples 1 to 3:
all the iron complexes have a dark color.

| Example | Aromatic diamine | Iron compound |
|---|---|---|
| 4 | o-phenylenediamine | iron(II)formiate |
| 5 | o-phenylenediamine | iron(II)glycolate |
| 6 | o-phenylenediamine | iron(III)propionate |
| 7 | o-phenylenediamine | iron(III)lactate |
| 8 | o-phenylenediamine | iron(III)oxalate |
| 9 | o-phenylenediamine | iron(II)malonate |
| 10 | o-phenylenediamine | iron(III)maleate |
| 11 | o-phenylenediamine | iron(III)succinate |
| 12 | o-phenylenediamine | iron(III)tartrate |
| 13 | o-phenylenediamine | iron(II)citrate |
| 14 | 4,5-dichloro-o-phenylenediamine | basic iron acetate |
| 15 | o-phenylenediamine | ferric hydroxide |
| 16 | 4-chloro-1,2-diaminobenzene | basic iron acetate |
| 17 | 4-chloro-1,2-diaminobenzene | iron carbonate |
| 18 | 4-chloro-1,2-diaminobenzene | ferrosoferric hydroxide |
| 19 | 4-chloro-1,2-diaminobenzene | ferric hydroxide |
| 20 | 4-methyl-1,2-diaminobenzene | iron carbonate |
| 21 | 4-methyl-1,2-diaminobenzene | ferrosoferric hydroxide |
| 22 | 4-methyl-1,2-diaminobenzene | ferric hydroxide |
| 23 | 4,5-dimethyl-1,2-diaminobenzene | iron oxalate |
| 24 | 4,5-dimethyl-1,2-diaminobenzene | basic iron acetate |
| 25 | 4,5-dimethyl-1,2-diaminobenzene | iron carbonate |
| 26 | 4,5-dimethyl-1,2-diaminobenzene | ferrosoferric hydroxide |
| 27 | 4,5-dimethyl-1,2-diaminobenzene | ferric hydroxide |

We claim:
1. Process for the production of an iron complex of a tetraazaannulene of the formula

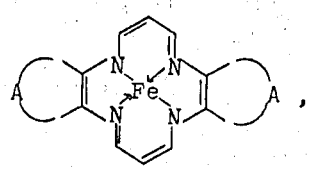

where A is 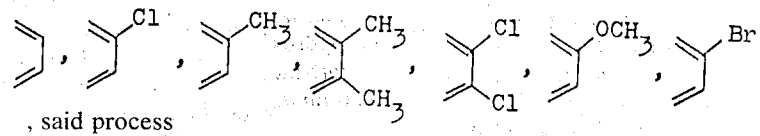, said process comprising the step of reacting one mole of isoxazole of the formula

with one mole of a diamine of the formula

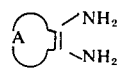

where A has the meaning given above, and with about ½ mole of an iron compound selected from the group consisting of:
  iron salts of organic mono- or dicarboxylic acids selected from the group consisting of formic, acetic, propionic, glyoxylic, lactic, malic, gluconic, oxalic, malonic, succinic, maleic, fumaric, tartaric and citric acid;
  iron acetyl acetonate;
  iron carbonate; and
  iron hydroxides.

2. Process according to claim 1, wherein basic iron acetylacetonate, iron carbonate, iron hydroxides, iron acetate, iron glycolate, iron tartrate, iron oxalate, iron citrate or iron lactate is used as the iron compound.

3. Process according to claim 1 wherein iron acetate is used as the iron compound.

* * * * *